United States Patent
Miller, II

(10) Patent No.: US 9,358,373 B2
(45) Date of Patent: *Jun. 7, 2016

(54) TRANSDERMAL PATCH INCORPORATING ACTIVE AGENT MIGRATION BARRIER LAYER

(71) Applicant: Mylan Technologies, Inc., St. Albans, VT (US)

(72) Inventor: Kenneth J. Miller, II, St. Albans, VT (US)

(73) Assignee: Mylan Technologies Inc, St. Albans, VT (US)

(*) Notice: Subject to any disclaimer, the term of this patent is extended or adjusted under 35 U.S.C. 154(b) by 125 days.

This patent is subject to a terminal disclaimer.

(21) Appl. No.: 14/278,486

(22) Filed: May 15, 2014

(65) Prior Publication Data

US 2014/0249492 A1   Sep. 4, 2014

Related U.S. Application Data

(63) Continuation of application No. 13/916,712, filed on Jun. 13, 2013, now Pat. No. 8,802,136, which is a continuation of application No. 10/641,654, filed on Aug. 15, 2003, now Pat. No. 8,524,272.

(51) Int. Cl.
   *A61M 35/00* (2006.01)
   *A61K 9/70* (2006.01)
   *A61F 13/02* (2006.01)

(52) U.S. Cl.
   CPC .............. *A61M 35/00* (2013.01); *A61K 9/703* (2013.01); *A61K 9/7084* (2013.01); *A61F 2013/0296* (2013.01)

(58) Field of Classification Search
   None
   See application file for complete search history.

(56) References Cited

U.S. PATENT DOCUMENTS

| | | |
|---|---|---|
| 4,466,953 A | 8/1984 | Keith et al. |
| 4,564,010 A | 1/1986 | Coughlan et al. |
| 4,573,996 A | 3/1986 | Kwiatek et al. |
| 4,588,580 A | 5/1986 | Gale et al. |
| 4,601,893 A | 7/1986 | Cardinal |
| 4,627,429 A | 12/1986 | Tsuk |
| 4,666,441 A | 5/1987 | Andriola et al. |
| 4,725,272 A | 2/1988 | Gale |
| 4,844,903 A | 7/1989 | Seth |

(Continued)

FOREIGN PATENT DOCUMENTS

| | | |
|---|---|---|
| EP | 0171800 A1 | 2/1986 |
| FR | 2375861 A1 | 7/1978 |

(Continued)

OTHER PUBLICATIONS

Supplementary European Search Report for Application No. EP 04705280, dated Feb. 8, 2012.

*Primary Examiner* — Isis Ghali

(57) ABSTRACT

Devices for administration of one or more active agents to the skin or mucosa of a host are formed in the nature of a double-disk patch. One outer layer functions as the primary adhesive layer for adhering the patch to the host. The other inner layer contains at least one active agent to be administered to the host. The inner layer is bonded to the outer layer through an opening provided in an interposed active agent impermeable release layer. The release layer separates a circumferential portion of the active agent containing inner layer from the outer adhesive layer to inhibit migration of the active agent therebetween.

15 Claims, 5 Drawing Sheets

(56) References Cited

U.S. PATENT DOCUMENTS

| | | |
|---|---|---|
| 4,849,224 A | 7/1989 | Chang et al. |
| 4,911,707 A | 3/1990 | Heiber et al. |
| 4,943,435 A | 7/1990 | Baker et al. |
| 4,983,395 A | 1/1991 | Chang et al. |
| 5,008,110 A | 4/1991 | Benecke et al. |
| 5,064,422 A | 11/1991 | Wick |
| 5,066,494 A | 11/1991 | Becher |
| 5,123,900 A | 6/1992 | Wick |
| 5,128,137 A | 7/1992 | Muller et al. |
| 5,149,538 A | 9/1992 | Granger et al. |
| 5,217,718 A | 6/1993 | Colley et al. |
| 5,284,660 A | 2/1994 | Lee et al. |
| 5,503,844 A | 4/1996 | Kwiatek et al. |
| 5,662,925 A | 9/1997 | Ebert et al. |
| 5,662,926 A | 9/1997 | Wick et al. |
| 5,738,647 A | 4/1998 | Bernhard et al. |
| 5,902,433 A | 5/1999 | Becher et al. |
| 5,932,240 A | 8/1999 | D'Angelo et al. |
| 5,948,433 A | 9/1999 | Burton et al. |
| 6,010,715 A | 1/2000 | Wick et al. |
| 6,096,333 A | 8/2000 | Rolf et al. |
| 6,171,294 B1 | 1/2001 | Southam et al. |
| 6,190,690 B1 | 2/2001 | Park et al. |
| 6,216,033 B1 | 4/2001 | Southam et al. |
| 6,274,166 B1 | 8/2001 | Sintov et al. |
| 6,277,401 B1 | 8/2001 | Bello et al. |
| 6,284,266 B1 | 9/2001 | Zhang et al. |
| 6,425,892 B2 | 7/2002 | Southam et al. |
| 6,471,986 B1 | 10/2002 | Cline et al. |
| 6,737,080 B1 | 5/2004 | Schumann |
| 2002/0177839 A1 | 11/2002 | Cormier et al. |
| 2003/0072792 A1 | 4/2003 | Flanigan et al. |
| 2003/0138479 A1 | 7/2003 | Mizota et al. |
| 2004/0043171 A1 | 3/2004 | Audett |
| 2004/0047901 A1 | 3/2004 | Beier et al. |
| 2004/0191301 A1 | 9/2004 | Van Duren |

FOREIGN PATENT DOCUMENTS

| | | |
|---|---|---|
| WO | 00/18338 | 4/2000 |
| WO | 03/030880 | 4/2003 |
| WO | 2005/004842 | 1/2005 |
| WO | 2005/025549 | 3/2005 |

TRANSDERMAL PATCH INCORPORATING ACTIVE AGENT MIGRATION BARRIER LAYER

CROSS-REFERENCE TO RELATED APPLICATIONS

This application is a continuation of U.S. application Ser. No. 13/916,712, filed on Jun. 13, 2013 which is a continuation of U.S. application Ser. No. 10/641,654, filed on Aug. 15, 2003, the disclosure of which is incorporated herein by reference.

FIELD OF THE INVENTION

The present invention relates in general to a device for the release of an active agent to be administered to the skin or mucosa of a host. More particularly, the present invention relates to transdermal patches which inhibit active agent migration by incorporating a releasable barrier layer.

BACKGROUND OF THE INVENTION

The use of transdermal patches for the delivery of various drug systems has met with increasing success in the pharmaceutical industry, particularly in view of specific problems which have arisen in connection with drugs taken by other means, and because of their implications in terms of long term application of drugs in a particular simple manner. One of the specific problems which has been encountered in connection with the use of various drugs has been the ability to apply a drug in a simple system which employs the drug in admixture with an adhesive base system for application to the skin, or non-adhesive base system having an outer drug permeable adhesive layer. The ability to do this with various types of drugs can be impeded by various considerations, such as differences in viscosity, solubility, therapeutic drug delivery rate, drug migration within the system, and the like.

Simple monolithic transdermal systems incorporate their active agents, i.e., drugs, directly into a single pressure sensitive adhesive layer. These systems have the advantage of being thin, elegant, and relatively easy to manufacture, but must compromise between optimizing the adhesive matrix for drug delivery versus its ability to adhere to the skin.

The known "double-disk" transdermal patch uses a larger auxiliary patch over a smaller active agent delivery patch to improve or ensure adhesion to the skin. The adhesive matrixes of the inner and outer patches can be independently optimized for active agent delivery and adhesion, respectively. When the inner and outer patches are laminated together to form the completed system, their adhesive matrixes come into direct contact and begin to equilibrate. As the systems equilibrate, time-dependent changes occur such as the loss of active agents from the inner patch and the simultaneous accumulation of active agents in the outer patch. This phenomenon can alter the performance of the transdermal patch if any of the components in the inner patch, especially those that are needed to achieve or sustain active agent delivery, have appreciable affinity for the outer patch adhesive matrix. Moreover, this effect will become more profound with time until equilibrium is achieved.

One solution in preventing the equilibrium of the two adhesive matrixes is to maintain their physical separation, and not to allow the adhesives to come into direct contact with each other during storage. Following application to the skin, these adhesive matrixes will be in direct contact, but the equilibrium process, typically two-three years, is slow compared to the transdermal delivery process, generally less than seven days. However, in the double-disk transdermal patch, the circumferential edge of the inner patch containing the active agent is exposed to the overlying outer patch and its adhesive matrix. This structure of the double-disk transdermal patch allows for the circumferential migration of active agent from the inner patch into the adhesive matrix of the outer patch.

SUMMARY OF THE INVENTION

The device of the present invention inhibits the migration of active agents between the inner and outer patches by maintaining a physical barrier between the patches during storage, i.e., prior to use by a patient. This allows the device to overcome the material compatibility limitations previously associated with double-disk type transdermal patches. Although the device of the present invention has specific application in transdermal patches, the device has general application for the release of an active agent to the skin or mucosa of a host. In this regard, the device has application in active agent delivery systems which include, but are not limited to, transmucosal, buccal, sub-lingual and medicated wound care.

The device of the present invention more broadly inhibits the migration of a component of the device, such as both active and non-active agents and other ingredients, including but not limited to non-active excipients, penetration enhancers, plasticizers, etc. between the inner and outer patches of the devise. In this regard, components included in the device of the present invention are inhibited from migration from the outer patch into the inner patch and from the inner patch into the outer patch.

The device of the present invention adheres the inner and outer patches in a manner to create an annular flap circumferentially about the outer portion of the inner patch. A disposable release liner is interposed between the annular flap and the adhesive material of the outer patch. The annular flap containing the active agent is isolated from the underlying portion of the outer patch by the release liner to inhibit active agent migration therebetween.

More specifically, the device of the present invention is in the nature of a double-disk system which includes an active agent containing inner patch permanently attached to an adhesive outer patch through an opening provided in a release liner for the outer patch. The inner patch includes an active agent impermeable backing layer, active agent layer containing the active agent to be delivered to the skin or mucosa of a host, which may also be an adhesive matrix layer and a disposable release liner. The outer patch includes a backing layer, adhesive matrix layer which may contain additional active agents, and a disposable release liner preferably of active agent impermeable material. The opening in the release liner of the outer patch exposes a portion of the outer patch adhesive matrix. The opening is smaller in size than the active agent inner patch, and provides an anchor point for the inner patch while preventing contact between the inner and outer patches prior to use.

In one embodiment of the present invention there is described a device for the release of an active agent to the skin or mucosa of a host, the device comprising an outer layer having adhesive properties; an inner layer having an active agent impermeable layer, the inner layer having a portion thereof adhered to the outer layer; and a release liner interposed between a portion of the impermeable layer and a portion of the outer layer, whereupon removal of the release liner exposes the outer layer for adhering the device to the skin or mucosa of a host.

In a further embodiment of the present invention there is described a device for the release of an active agent to the skin or mucosa of a host, the device comprising a first layer having adhesive properties adapted for adhering said first layer to the skin or mucosa of a host; a second layer releasably adhered to the first layer, the second layer having an opening exposing a portion of the first layer; and a third layer overlying the second layer, the third layer including an active agent impermeable layer having a portion thereof adhered to the first layer within the opening in the second layer, the second layer separating a portion of the third layer from the first layer prior to removal of the second layer when adhering the device to the skin or mucosa of a host by the first layer.

In a further embodiment of the present invention there is described a device for the release of an active agent to the skin or mucosa of a host, the device comprising an outer layer having top and bottom surfaces, the top surface of the outer layer having adhesive properties adapted for adhering the outer layer to the skin or mucosa of a host; a liner releasably adhered to the top surface of the outer layer, the liner having an opening exposing a portion of the top surface of the outer layer; an active agent inner layer having an active agent overlying the liner, the inner layer having a surface area smaller than a surface area of the outer layer and greater than a surface area of the opening in the liner; and an active agent impermeable layer adhered to the bottom surface of the inner layer, the impermeable layer having a portion thereof adhered to the top surface of the outer layer within the opening in the liner, whereby a portion of the liner is interposed between a portion of the inner layer and a portion of the outer layer to inhibit migration of the active agent from the inner layer to the outer layer prior to adhering the device to the skin or mucosa of a host upon removal of the liner.

In a further embodiment of the present invention there is described a method for inhibiting migration of a component of an active agent release device between an inner layer and an adhesive outer layer within the device prior to adhering the device to the skin or mucosa of a host, the inner layer having a component impermeable layer partially adhered to the outer layer, the method comprising interposing a release liner between a peripheral portion of the inner layer and the outer layer.

In a further embodiment of the present invention there is described a method for inhibiting migration of an active agent from an active agent inner layer into an adhesive outer layer within an active agent release device prior to adhering the device to the skin or mucosa of a host, the inner layer having an active agent impermeable layer, the method comprising adhering a release liner to a first portion of the outer layer; and adhering a portion of the impermeable layer of the inner layer to a second portion of the outer layer, whereby a remaining portion of the impermeable layer is arranged overlying the release liner, the release liner separating a peripheral portion of the inner layer from the outer layer until removal of the release liner.

In a further embodiment of the present invention there is described a method of making a device for the release of an active agent to the skin or mucosa of a host, the method comprising adhering a portion of an active agent impermeable layer of an inner layer to an outer layer having adhesive properties; and interposing a release liner between a portion of the impermeable layer and the outer layer, whereupon removal of the release liner exposes the outer layer for adhering the device to the skin or mucosa of a host.

In a further embodiment of the present invention there is described a method of making a device for the release of an active agent to the skin or mucosa or a host, the method comprising providing a first layer having adhesive properties adapted for adhering the first layer to the skin or mucosa of a host; releaseably adhering a second layer to the first layer, the second layer having an opening exposing a portion of the first layer; overlying a third layer with the second layer, the third layer including an active agent impermeable layer; and adhering a portion of the impermeable layer to the first layer within the opening in the second layer, the second layer separating a portion of the third layer from the first layer prior to removal of the second layer when adhering said device to the skin or mucosa of a host by the first layer.

In a further embodiment of the present invention there is described a method of making a device for the release of an active agent to the skin or mucosa of a host, the method comprising providing an outer layer having top and bottom surfaces, the top surface of the outer layer having adhesive properties adapted for adhering the outer layer to the skin or mucosa of a host; releaseably adhering a liner to the top surface of the outer layer, the liner having an opening exposing a portion of the top surface of the outer layer; positioning an active agent inner layer having an active agent impermeable layer overlying the liner, the inner layer having a surface area smaller than a surface area of the outer layer and greater than a surface area of the opening in the liner; and adhering a portion of the impermeable layer to the top surface of the outer layer within the opening in the liner, whereby a portion of the liner is interposed between a portion of the inner layer and a portion of the outer layer to inhibit migration of the active agent from the inner layer to the outer layer prior to adhering the device to the skin or mucosa of a host upon removal of the liner.

In a further embodiment of the present invention there is described a method for inhibiting migration of a component of an active agent release device between an inner layer and an adhesive outer layer within the device prior to adhering the device to the skin or mucosa of a host, at least one of the inner layer and the outer layer including the component, the inner layer having a component impermeable layer partially adhered to the outer layer within a bonding region, the method comprising interposing a release liner between a peripheral portion of the inner layer surrounding the bonding region and the outer layer.

BRIEF DESCRIPTION OF THE DRAWINGS

The subject matter regarded as the invention is particularly pointed out and distinctly claimed in the concluding portion of the specification. The invention, however, both as to organization and method of operation, together with features, objects, and advantages thereof may best be understood by reference to the following detailed description when read with the accompanying drawings in which:

DETAILED DESCRIPTION OF THE PREFERRED EMBODIMENTS

Figure 1:
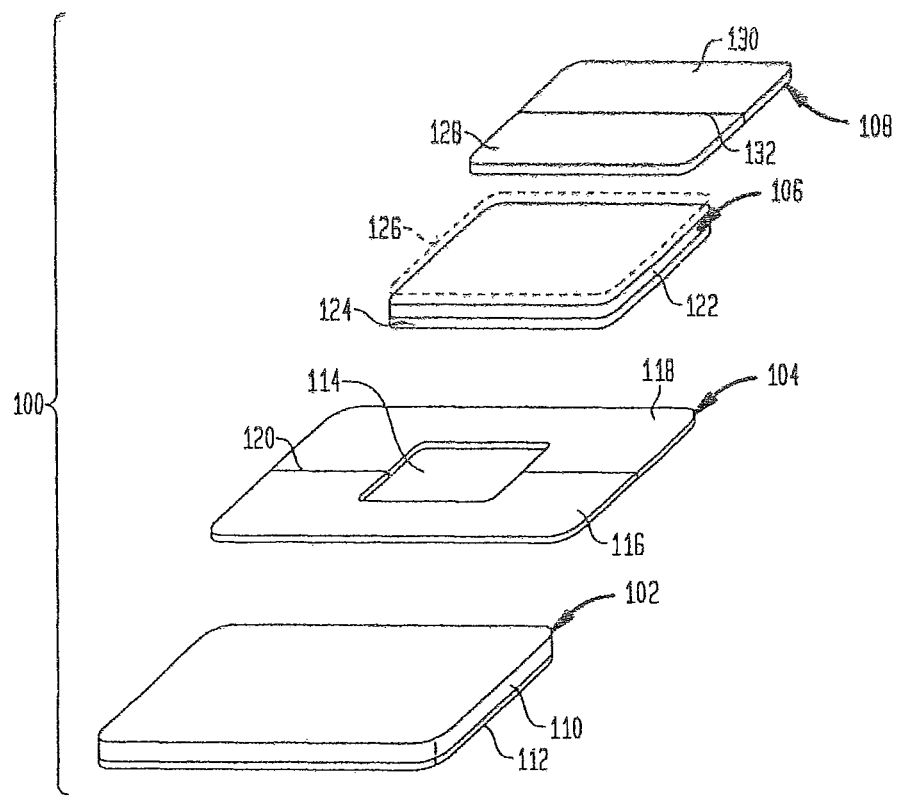
FIG. 1 is a perspective unassembled exploded view of the components of a device for the release of an active agent for application to the skin or mucosa of a host in accordance with one embodiment of the present invention.

In describing the preferred embodiments of the invention illustrated in the drawings, specific terminology will be used for the sake of clarity. However, the invention is not intended to be limited to the specific terms so selected, and it is to be understood that each specific term includes all technical equivalents that operate in a similar manner to accomplish a similar purpose.

Referring now to the drawings, wherein like elements represent like elements, there is shown in FIG. 1 the unassembled components of a device for the administration of one or more active agents to the skin or mucosa of a host in accordance with one embodiment of the present invention. The device 100 generally includes an outer patch 102, an outer patch release layer 104, an inner patch 106 and an inner patch release layer 108. The outer and inner patches 102, 106 and release layers 104, 108, which are typically planar layers, are assembled to one another to form a laminate composite structure in the nature of a double disk device as to be described hereinafter.

The outer patch 102 includes a flexible adhesive layer 110 and a co-extensive protective backing layer 112 adhered thereto. The adhesive layer 110 provides the primary adhesion of the device 100 to the skin or mucosa of a host. Preferably, the adhesive layer 110 is a pressure-sensitive adhesive suitable for contact with the skin or mucosa of a host, e.g., dermatologically acceptable. Optionally, the adhesive layer may be admixed with an active agent or other drug to be administered to a host. In which case, the adhesive layer 110 will be formed from active agent permeable material to allow administration of the active agent.

The backing layer 112 is preferably a thin sheet which is co-extensive with the bottom surface of the adhesive layer 110. Because of the area of skin to which the device 100 is to be attached, the backing layer 112 may be flesh-colored for cosmetic reasons. The backing layer 112 normally provides support and a protective covering for the device 100. The backing layer 112 may be formed from a sheet of active agent impermeable or permeable material. Preferably, the backing layer 112 will be formed from active agent impermeable material when an active agent is present in the adhesive layer 110.

The outer patch release layer 104 covers the top surface of the adhesive layer 110 prior to use of the device 100 to protect the adhesive layer from inactivation by ambient dust or other contaminants and to provide an active agent migration barrier as to be described. The release layer 104 has a sufficient surface area and shape to extend at least to the peripheral edges of the adhesive layer 110. An opening 114 within the release layer 104 exposes a portion of the top surface of the adhesive layer 110 of the underlying outer patch 102. The release layer 104 may be formed as a single sheet of material, or multiple sections 116, 118 which are separated by one or more slits 120. Preferably, the release layer 104 is formed from a sheet of active agent impermeable material thereby providing a migration barrier to the active agents in the inner patch 106.

The inner patch 106 includes a flexible active agent layer 122 and a co-extensive active agent impermeable backing layer 124 adhered to the bottom surface thereof. The active agent layer 122 may be formed from a thermoplastic polymeric matrix which is admixed with the active agent or drug components, and optionally, an active agent enhancer. The polymeric matrix for the active agent layer 122 preferably has pressure-sensitive adhesive properties, or in the alternative, the active agent layer may be coated with an active agent permeable adhesive layer 126 as shown in phantom. It is not a requirement of the present invention that the active agent layer 122 have adhesive properties or be provided with an adhesive layer. In this regard, the device 100 will be adhered to the host primarily by the adhesive layer 110 of the outer patch 102. The active agent layer 122, when having adhesive properties, will add to the adhesion of the device 100 to a host.

The inner patch release layer 108 may be formed as a similar sheet as release layer 104 from one or more sections 128, 130 separated by a slit 132. The release layer 108 has a surface area and shape to at least extend to the perimeter of the top surface of the active agent layer 122. The release layer 108 covers the top surface of the active agent layer 122 prior to use of the device 100 to prevent the release of the active agent. When the active agent layer 122 has pressure-sensitive adhesive properties, or is covered with an active agent permeable adhesive layer, the release layer 108 provides protection from inactivation by ambient dust or other contaminants.

Figure 2:
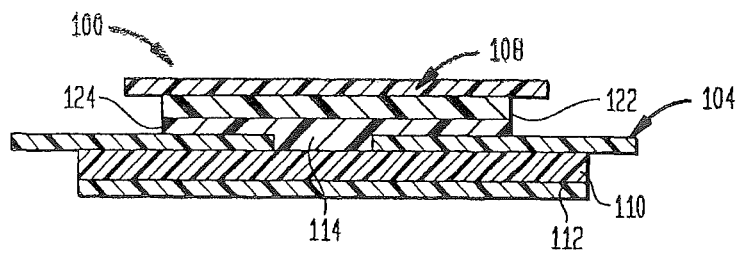
FIG. 2 is an assembled cross-sectional view of the device shown in FIG. 1.
Figure 3:
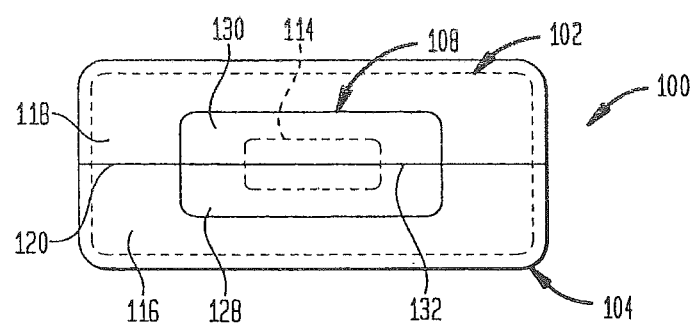
FIG. 3 is a top plan view of the device shown in FIG. 1.

The device 100 is shown in assembled relationship in FIGS. 2 and 3 in the nature of a laminate composite device of generally planar layers. The release liner 104 is releasably adhered in co-extensive contact with the top surface of adhesive layer 110 of the outer patch 102. The opening 114 in release layer 104 exposes a portion of the top surface of the underlying adhesive layer 110. The inner patch 106 is adhered to the outer patch 102 by bonding the impermeable backing layer 124 to the adhesive layer 110 exposed within the opening 114. The surface area of the opening 114 is smaller than the surface area of inner patch 106. This results in the inner patch 106 having an annular portion in the nature of a flap surrounding opening 114, which is not bonded to the adhesive layer 110 as a result of an interposed portion of the release liner 104. Likewise, the peripheral edges of the active agent layer 122 are separated from the adhesive layer 110 by a portion of the release liner 104. The impermeable backing layer 124 and impermeable release layer 104 isolate the active agent layer 122 to inhibit migration of an active agent from the active agent layer to the adhesive layer 110 during storage of the device 100 prior to use.

The device 100 is prepared for application to the skin or mucosa of a host by removing release layers 104, 108. To facilitate removal of release layer 104, it is preferable that at least a portion of the release layer extend beyond the periphery of the underlying adhesive layer 110. The extended portion may be in the nature of a tab or annular portion circumscribing the entire perimeter or portion of the adhesive layer 110 as shown in FIG. 3. In this manner, each section 116, 118 of the release layer 104 may be removed to expose the top surface of the adhesive layer 110 surrounding the inner patch 106 containing the active agent. The exposed surface portion of the adhesive layer 110 will have sufficient surface area to provide adhesion of the device 100 to the skin or mucosa of a host during use. Removal of the sections 116, 118 are undertaken individually as a result of their separation by slit 120. This enables removal of the sections 116, 118 notwithstanding a portion of the sections surrounding the opening 114 being interposed between the adhesive layer 110 and impermeable backing layer 124 of the inner patch 106.

Figure 4:
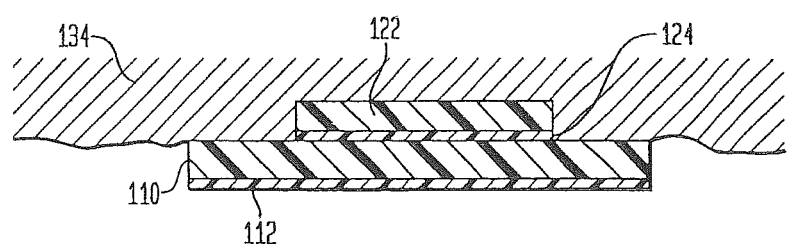
FIG. 4 is a cross-sectional view of the application of the device shown in FIG. 2 adhered to the skin or mucosa of a host.

In a like manner, the release layer 108 is removed from the top surface of the active agent layer 122 by grasping an extended portion of sections 128, 130. The device 100 is adhered to the skin or mucosa of a host 134 as shown in FIG. 4 with the active agent layer 122 in contact with the host. The host to which an active agent is administered by means of the inventive device may be any host on which a drug or other active agent has the desired effect. The host may be, for example, a mammal such as a human being, or, for that matter, any warm-blooded or cold-blooded animal. The advantage of administering the active agent may be therapeutic or experimental. The device 100 of this invention may also be used for any other advantageous purpose.

The extended sections of the release layer 108 may be as described with respect to release layer 104. However, it is to be understood that it is not required that the release layers 104, 108 extend beyond the periphery of their underlying adhesive layer 110 and active agent layer 122, respectively. The extension of the release layers 104, 108 merely facilitates removal of the release layers by the user prior to application of the device 100.

The individual components of the device 100 have been illustrated as being rectangular in shape for illustrative purposes only. It is to be understood that the device 100 and its components may have any other shape, such as square, round, oval and the like. For example, the outer patch 102 may have a square shape, while the inner patch 106 may be circular. In addition, it is not a requirement of the present invention that opening 114 be rectangular, and may be formed as a plurality of non-contiguous openings within the release layer 104. The opening 114 serves one function of enabling bonding of the inner patch 106 to the outer patch 102 in assembling the device 100. In addition, the surface area of opening 114 in relationship to the surface area of the inner patch 108 defines the extent of the circumferential portion of the inner patch which is separated from the adhesive layer 110 by the interposed release layer 104. Accordingly, the size, shape and location of the opening 114 can be tailored to accommodate the migration of an active agent based upon, for example, the migration rate of the active agent within the active agent layer 122.

Figure 5:
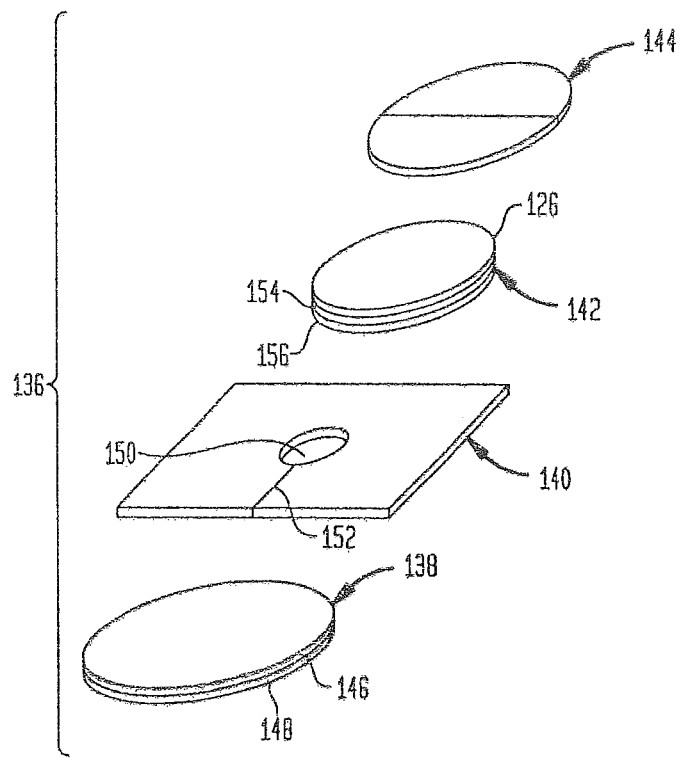
FIG. 5 is a perspective unassembled exploded view of the components of a device for the release of an active agent for application to the skin or mucosa of a host in accordance with another embodiment of the present invention.
Figure 6:
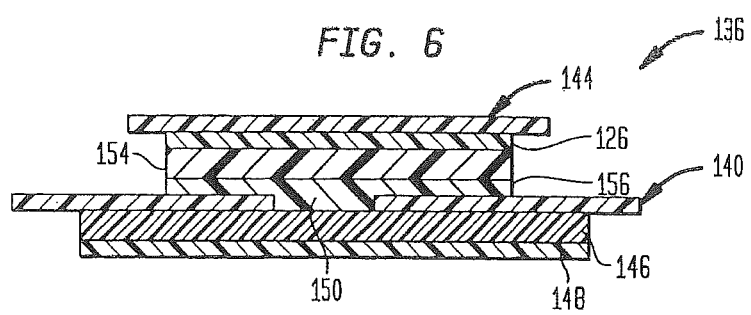
FIG. 6 is an assembled cross-sectional view of the device shown in FIG. 5.
Figure 7:
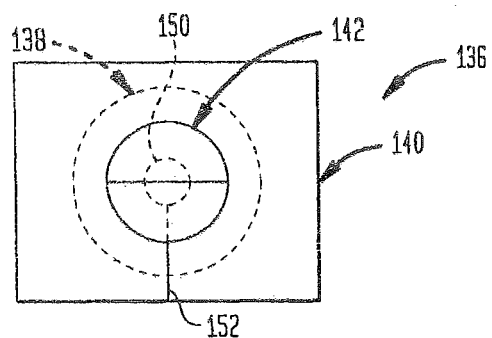
FIG. 7 is a top plan view of the device shown in FIG. 6.

Referring to FIGS. 5-7, there is disclosed another embodiment of a device 136 adapted for the administration of an active agent to the skin or mucosa of a host. The device 136 differs in one aspect from the device 100 in the shape of its component parts. In this regard, the device 106 includes a circular outer patch 138, a square or rectangular outer patch release layer 140, a circular inner patch 142 and a circular inner patch release layer 144.

The outer patch 138 includes an adhesive layer 146 and a co-extensive outer backing layer 148. The adhesive layer 146 may be in the nature of a pressure-sensitive adhesive, and optionally, admixed with an active agent or other drug to be administered to a host. In this event, the backing layer 148 will be in the nature of a sheet of active agent impermeable material.

The release layer 140, like release layer 104, is preferably formed from a sheet of active agent impermeable material which is releasably adhered to the top surface of the adhesive layer 146 of the outer patch 138. The release layer 140 includes an opening 150 which exposes a portion of the top surface of the adhesive layer 146 through which the inner patch 142 is adhered. Removal of the release layer 140 is facilitated by a slit 152 extending from an outer edge of the release layer to the opening 150.

The inner patch 142 includes an active agent layer 154 which may be a mixture of polymeric materials along with the active agent or other ingredients so as to possess pressure-sensitive adhesive properties for adhering the device 136 to the skin or mucosa of a host. However, it is not a requirement that the active agent layer 154 have adhesive properties. In this regard, the top surface of the active agent layer 154 can be coated with an active agent permeable adhesive layer 126. It is also contemplated, although not shown, that the inner patch 142 may include a rate-controlling polymer layer to provide a means for controlling the rate at which the active agent is released from the surface of the inner patch 142 to the skin or mucosa of the host. The rate-controlling polymer layer may be adhered to the surface of the active agent layer 154 using any suitable active agent permeable adhesive such as that used for adhesive layer 126.

The inner patch 142 further includes an active agent impermeable backing layer 156 adhered to the bottom surface of the active agent layer 154. The impermeable backing layer 156 may be adhered using the pressure-sensitive adhesive properties of the active agent layer 154, or by a layer, not shown, of preferably an active agent impermeable adhesive. The release layer 144, similar to release layer 108, is releasably adhered to the top surface of the inner patch 142 for preventing release of the active agent and for protecting and preventing contamination to the adhesive properties of the inner patch.

A portion of the release layer 140 is interposed between a portion of the bottom surface of the inner patch 142 and the top surface of the adhesive layer 146 of the outer patch 138. The inner patch 142 is formed with an annular flap circumscribing the opening 150 of the release layer 140 which is isolated from the adhesive layer 146 by the release liner to prevent migration of the active agent therebetween. Upon removal of the release layer 140, an annular portion of the top surface of the adhesive layer 146 is exposed surrounding the perimeter of the inner patch 142. The adhesive layer 146 provides sufficient adhesion to adhere the device 136 to the skin or mucosa of a host. The adhesion of the device 136 is enhanced by the inner patch 142 having either pressure-sensitive adhesion properties or the incorporation of an active agent permeable adhesive layer 126. However, it is contemplated that the inner patch 142 will be devoid of adhesive properties, relying solely upon the adhesive properties of the outer patch 138 to provide adhesion of the device 136 to the skin or mucosa of a host.

As previously described, the active agent or drug is contained within the active agent layer 122, 154, and optionally in the adhesive layer 110, 146. The active agent may be, for example, systemic or topical drugs. Individual active agents or mixtures thereof, if desired, can be employed. Any drug which passes through the skin or mucosa of a host can be employed for internal administration in the device of the invention so long as the drug will pass through the permeable adhesive layer or layers present. The active agent and thermoplastic matrix polymer can be melt-blended in an extruder and then formed into the active agent layer 122, 154 or adhesive layer 110, 146 by extrusion. Other known processes for incorporation of the active agent such as solvent blending are contemplated.

Suitable systemic drugs for administration by the devices of the present invention include psychoactive agents such as nicotine, caffeine, mesocarb, mefexamide, cannabinols such as THC, and the like, sedatives such as diazepam, mepiridine, uldazepam, tybamate, metaclazepam, tetrabarbitol and the like, antidepressants such as amitryptyline, imipramine desipramine, nialamide, melitracen, isocarboxazid, and the like, anticonvulsants such as phenobarbitol, carbamazepine, methsuximide, 2-ethyl-2-phenylmalonamide (PEMA), phenytoin and the like, steroids such as progesterone, testosterone, pregnanediol, progestin, estradiol, anabolic steroids and the like, analgesics, including narcotic analgesics such as codeine, morphine, fentanyl, analorphine, demeral and the like, and analgesics such as acetaminophen, aspirin, and the like, antimicrobial agents such as sulconazole, siccanin, silver sulfadiazine, bentiacide, and the like, tranquilizers such as alprazolam, meprobamate and the like, antineoplastic agents such as sulfosfamide, rufocromomycin and the like, and antibiotic agents such as tetracycline, penicillin, streptozcin and the like.

The quantity of active agent present is that quantity sufficient to provide a pharmaceutically or physiologically effective dosage rate of the active agent to a host in need thereof. This quantity can be readily determined by those of ordinary skill in the art without undue experimentation as shown in the examples set forth below.

The device 100, 136 of the present invention optionally include a rate-controlling polymer layer. The polymers suitable for use as the rate-controlling polymer layer are conventional in the art and need not be discussed in detail here. Some preferred materials include, for example, polyethylene, polypropylene, ethylene vinyl acetate copolymer (EVA), copolyesters (e.g., HYTREL) and polyurethanes.

The rate of permeation of the active agent through the rate-controlling polymer layer depends on factors such as the affinity of the active agent for the polymer layer, molecular size of the active agent, polymeric structure of the carrier layer and the thickness of the layer. Therefore, the appropriate rate-controlling polymeric material and its thickness depend on the active agent used and the desired rate of permeation. The selection of a polymer layer and its thickness provides a means, if desired, for controlling the dosage rate to the skin or mucosa.

Further, an enhancer to promote the penetration of the active agent through the skin may be included in either the active agent layers 122, 154, rate-controlling polymer layers or the active agent permeable adhesive layers, if present. The enhancer may be incorporated into these layers by solvent blending or, more preferably, by melt-blending by the same process utilized to incorporate the active agent into either the active agent layers 122, 154 or the adhesive layers 110, 146, which adhesive layers may also include an enhancer.

Suitable enhancers include those described in U.S. Pat. No. 4,573,996, such as the following enhancers: monovalent, saturated and unsaturated aliphatic and cycloaliphatic alcohols having 6 to 12 carbon atoms such as cyclohexanol, lauryl alcohol and the like; aliphatic and cycloaliphatic hydrocarbons such as mineral oils; cycloaliphatic and aromatic aldehydes and ketones such as cyclohexanone; N,N-di (lower alkyl) acetamides such as N,N-diethyl acetamide, N,N-dimethyl acetamide, N-(2-hydroxyethyl) acetamide, and the like; aliphatic and cycloaliphatic esters such as isopropyl myristate and lauricidin; N,N-di (lower alkyl) sulfoxides such as decylmethyl sulfoxide; essential oils; nitrated aliphatic and cycloaliphatic hydrocarbons such as N-methyl-2-Pyrrolidone, Azone; salicylates, polyalkylene glycol silicates; aliphatic acids such as oleic acid and lauric acid, terpenes such as cineole, surfactants such as sodium lauryl sulfate, siloxanes such as hexamethyl siloxane; mixtures of the above materials; and the like.

The backing layer 124, 156 is preferably made of a material or combination of materials that is substantially impermeable to the layer or layers with which it can be in contact, e.g., to the active agent layers 122, 154, the adhesive layer 110, 146 and the active agents or ingredients contained therein, the adhesives, etc. In this regard, a primary objective is to prevent migration or seepage of the active agents or ingredients through the backing layer 124, 156 of the inner patch 106, 142 into the underlying adhesive layer 110, 146. The backing layer 112, 148 may also be made from a similar material being impermeable to the active agents, particularly when the active agents are present also within the adhesive layer 110, 146. The backing layer 112, 148 is not required to be impermeable to the active agents, particularly when there are no active agents in the adhesive layer 110, 146. Thus, it is not necessary in all instances that the backing layer 112, 148 be impermeable to the active agents, although in most instances it normally is.

By impermeable, it is meant that the other components in contact with the backing layer or component under consideration will not appreciably permeate through such layer or component for the normal period of use and storage of the device. Some suitable materials for the backing layer include, for example, cellophane, cellulose acetate, ethyl cellulose, plasticized vinyl acetate-vinyl chloride copolymers, ethylene-vinyl acetate copolymer, polyethylene terephthalate, polyvinyl chloride, nylon, polyethylene, polypropylene and polyvinylidene chloride (e.g., SARAN).

Examples of suitable pressure-sensitive-adhesive materials for use in the present invention as an active agent impermeable adhesive include some natural rubber and synthetic rubber adhesives and cross-linkable laminating adhesives. Examples of suitable natural rubber adhesives include R-1072 from B.F. Goodrich Co., No. 735 from C.L. Hathaway, and No. 5702 from Evans St. Clair. Examples of synthetic rubber adhesives include Jowatherem 270-00 and Jowatherem S-3202 from Jowat Corp. and 70-9416 from National Starch. Other suitable laminating adhesives include the Dow Corning laminating silicone adhesives and the Lord Corporation Tycel 7900 series laminating adhesives. Also contemplated are acrylic copolymers such as those available from National Starch and Chemical Co. of Bridgewater, New Jersey under the marks DURO-TAK 87-2516 and DURO-TAK 87-2287. The adhesives most impermeable to most active ingredients are cross-linkable laminating adhesives, which are well-known to those of ordinary skill in the art.

The active agent permeable adhesive layers are preferably a pressure-sensitive adhesive. Any of the well-known, dermatologically acceptable, pressure-sensitive adhesives which permit drug migration therethrough can be used in the present invention. Some suitable permeable adhesives include acrylic or methacrylic resins such as polymers of alcohol esters of acrylic or methacrylic acids and alcohols such as n-butanol, isopentanol, 2-methylbutanol, 1-methyl-butanol, 1-methylpentanol, 2-methylpentanol, 3-methylpentanol, 2-ethyl-butanol, isooctanol, n-decanol, or n-dodecanol, alone or copolymerized with ethylenically unsaturated monomers such as acrylic acid, methacrylic acid, acrylamide, methacrylamides, N-alkoxymethyl acrylamides, N-alkoxymethyl methacrylamides, N-t-butyl-acrylamide, itaconic acid, vinyl acetate, N-branched alkyl maleamic acids wherein the alkyl group has 10-24 carbon atoms, glycol diacrylates, or mixtures of these monomers; polyurethane elastomers; vinyl polymers such as polyvinyl alcohol, polyvinyl ethers, polyvinyl pyrrolidone, and polyvinyl acetate; urea formaldehyde resins; phenol formaldehyde resins, resorcinol formaldehyde resins; cellulose derivatives such as ethylcellulose, methylcellulose, nitrocellulose, cellulose acetate butyrate and carboxymethylcellulose; and natural gums such as guar, acacia, pectina, starch, destria, gelatin, casein, etc.

Other suitable pressure-sensitive adhesives include polyisobutylene pressure sensitive adhesives, rubber pressure-sensitive adhesives and silicone pressure-sensitive adhesives.

The adhesives may also be compounded with tackifiers and stabilizers as is well-known in the art.

Adhesives that are preferred for their active agent permeability include acrylic copolymer adhesives such as Avery Chemical Company's AS-351 HSX, preferably at a coating weight of between 75 and 125 g/m$^2$. This pressure-sensitive adhesive is a cross-linkable polymer which provides a permanently tacky film having a total solids content of about 52%, Brookfield viscosity (LVT/Spindle No. 4/12 RPM @ 25'C) of from about 15,000 to 25,000 cps. at a weight per gallon of about 7.4 lbs. It can also be diluted with hexane or toluene to a desired solids and/or viscosity range, particularly for use in conventional coating equipment.

Other such adhesives that can also be used for these purposes include an acrylic pressure-sensitive adhesive sold by National Starch and Chemical Co. under the designation DURO-TAK 80-1054. This adhesive has a solids content of 47.5%, a viscosity of 3,000 cps., and plasticity (Williams) of 2.9 mm. It is generally used with a solvent system including ethyl acetate, heptane, isopropyl alcohol and toluene. Another such adhesive is sold by the UCB Group under the designation GELVA Multipolymer Emulsion 2484, and comprises a stable aqueous acrylic emulsion pressure-sensitive adhesive having a solids content of 59% and a viscosity of 1,500 to 2,300 cps. Examples of other acrylic adhesives include Gelva 788 and 733 from UCB, PS-41 from C.L.-Hathaway, Vr-0833 from H.B. Fuller, Adcot 73A207A from Morton Chemical, Nos. 80-2404, 80-1054, 72-9056 and 72-9399 from National Starch, Nos. E-2015, E-2067 and E-1960 from Rohm & Haas, M-6112 from Uniroyal, Inc. and Daratak 74 L from W.R. Grace. Suitable rubber adhesives include Duro-Tak 36-6172 from National Starch and Morstik 118 from Morton Chemical. An example of a suitable silicone adhesive is 7-4502 from Dow Corning.

The width (i.e., surface area) and thickness of the permeable adhesive layer for contact with the skin or mucosa is that width and thickness which provides sufficient permeability to the active agent or active agent enhancer and a suitable surface area to allow the dosage rate desired to the skin or mucosa. These widths and thicknesses are conventional in the art and therefore need not be discussed in detail here.

The active agent layers 122, 154 are preferably monolithic polymeric active agent carrier layers. Thus, in essence, these monolithic active agent carrier layers basically comprise a thermoplastic polymeric matrix which are admixed via melt-blending with the active agent or drug component or active agent enhancer, or both. However, monolithic polymer matrix carrier layers which blend the active agent with a matrix polymer in a common solvent and then evaporate the solvent to form a plastic film are contemplated. As is readily understood by those of ordinary skill in the art, the step of melt-blending requires the use of a thermoplastic polymer, that is, one that softens and melts when exposed to heat and then returns to its original condition when cooled. Suitable thermoplastic matrix polymers are the thermoplastic polyurethanes. Of this class, the polyether polyurethanes are preferred. These include such commercial polyurethane compositions such as Dow Chemical Company's PELLETHANE, including its 2363-80 AE grade thereof; K.J. Quin's Q-THANE; B.F. Goodrich's ESTANE; Mobay Chemical Company's TXIN; and others.

Suitable thermoplastic matrix polymers also include various polyesters, such as the copolymers of various cyclic polyesters including DuPont's HYTREL, including its 4056 grade thereof, and General Electric's LOMOD both of which are copolymers of polyether prepolymers and polybutylene terephthalate and polyisobutylene terephthalate, respectively, as well as Eastman Chemical's PCCE. Other suitable polymers include ethylene methacrylic and acrylic acid copolymers. For example, ethylene methacrylic acid having the commercial designation NUCREL 699 is particularly suitable as a thermoplastic matrix polymer.

The device 100, 136 include a release liner attached to the device such as at the surfaces to be adhered to the skin or mucosa of a host. The release liner may be made of the same materials suitable for use in the backing layer provided they are active agent impermeable. Such materials as a release liner are made removable or releasable from the adhesive layers or active agent layers by, for example, conventional treatment with silicon, Teflon or other suitable coating on the surface thereof. The removal of the device 100, 136 from the release liner may also be provided by mechanical treatment of the protective layer, e.g., by embossing the protective liner.

The various layers of the device 100, 136 of the present invention may be combined to form a laminate by methods conventional in the art. One such process includes combining the active agent and a thermoplastic matrix polymer by melt-blending the two components forming the polymer layers by extrusion. Another known process is referred to as a solvent-blend process using solvated components which form an admixture that is coated onto a substrate such as a release liner and subsequently dried. The melt-blending process is described in further detail in U.S. Pat. No. 6,010,715, the disclosure of which is incorporated herein by reference.

There is also known various materials for use in the construction of the device 100, 136 of the present invention for the backing layers, release layers, adhesive layers, active agent layers, pressure-sensitive adhesive layers, active agent permeable adhesive layers, active agent impermeable adhesive layers, active agent impermeable layers, active agent permeable adhesive layers, etc. Suitable materials are disclosed in U.S. Pat. Nos. 5,064,422, 5,123,900, 5,503,844 and 5,948,433, the disclosures of which are incorporated herein by reference.

Figure 8:
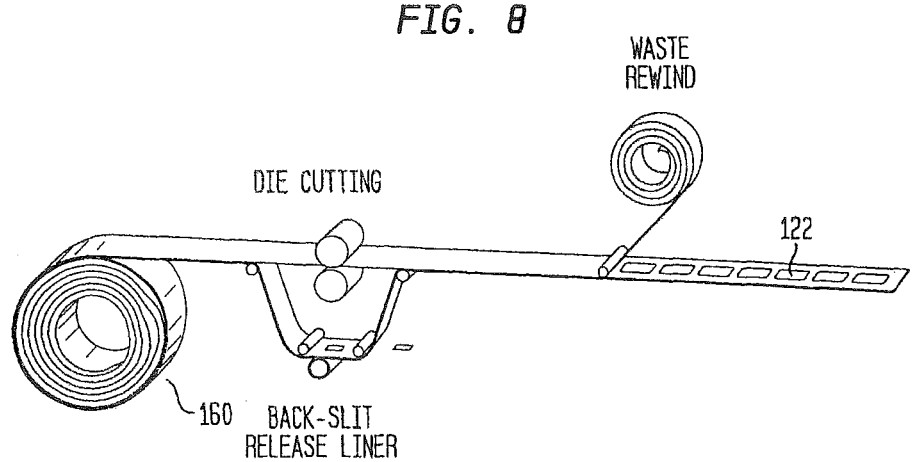
FIGS. 8-10 are diagrammatic illustrations of one embodiment a method of forming devices in accordance with the present invention.
Figure 9:
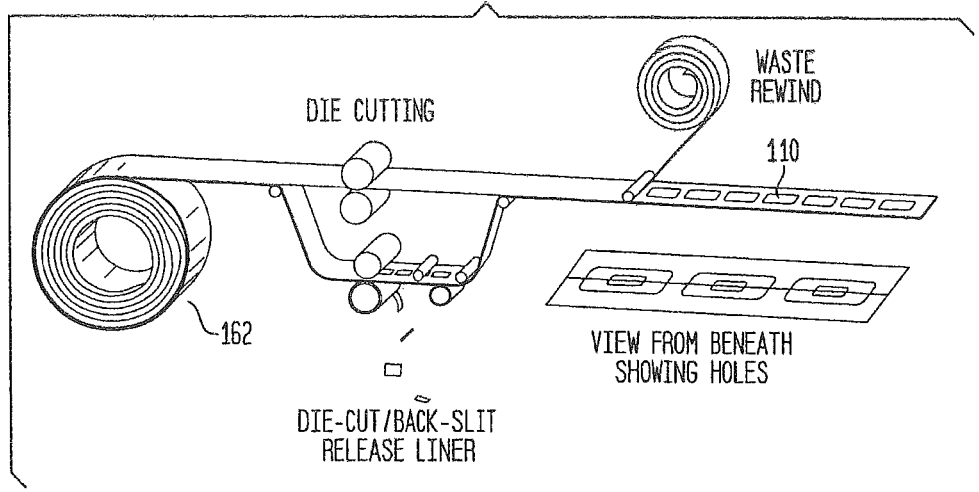
Figure 10:
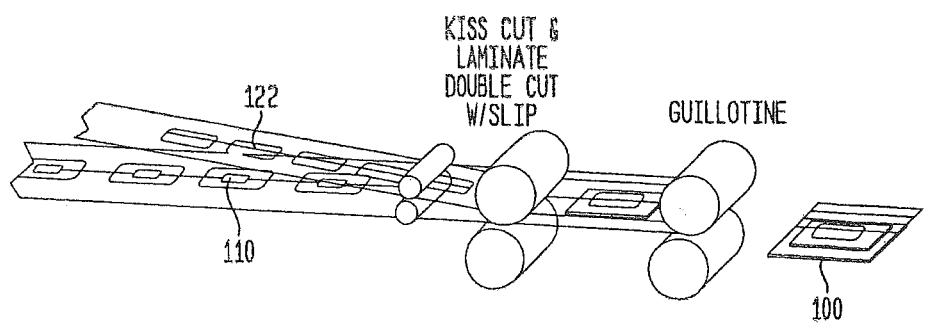

Referring to FIGS. 8-10, there is illustrated one example of a method of manufacturing the device 100, 136 via a solvent-blending process. With reference to the device 100, the active agent layer 122 is formed by admixing solvated polymer materials such as those having pressure-sensitive adhesive properties in conjunction with the active agent to be administered to the skin or mucosa of a host. The active agent polymeric admixture is coated onto a release liner, dried, laminated with an active agent impermeable backing layer, and wound into a continuous supply roll 160. The release liner is separated from the active agent layer and back slit to form slit 132 while the active agent layer is die cut to the desired size and shape of the inner patch 106. The release liner and active agent layer are re-joined, followed by removal of the extraneous active agent layer.

In a similar solvent-blending process as shown in FIG. 9, the pressure-sensitive adhesive matrix materials forming the adhesive layer 110 are coated onto a release liner, dried, laminated with a backing layer, and wound to form a supply roll 162. The release liner is removed from the adhesive layer, die cut to form opening 114 and back slit to form slit 120. The release liner is re-joined with the adhesive layer, followed by the removal of the waste adhesive layer.

Referring to FIG. 10, the supported active agent layer 122 is aligned overlying and in registration with the supported adhesive layer 110, and adhered thereto through the opening in the release liner in a continuous process. The release liner for the active agent layer is cut to appropriate size and shape, followed by a guillotine process for severing the outer patch release layer to form the completed device 100.

It is to be understood that the above description of a method of making the device 100, 136, as described with reference to FIGS. 8-10, is by way of one illustrative example only. In this regard, it is contemplated that other methods for manufacturing the device 100, 136 are contemplated, and accordingly, the described method is not to be interpreted as any limitation upon the scope of the present invention.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A storage-stable device for the release of an active agent to the skin or mucosa of a host, the device comprising:
    an outer patch including an adhesive layer;
    an outer patch release layer of an active agent impermeable material releasably adhered to the adhesive layer of the outer patch, the outer patch release layer including an opening exposing a portion of the adhesive layer, the outer patch release layer being removable prior to the application of the device to the skin or mucosa of a host;
    an inner patch comprising an active agent layer supported on an active agent impermeable backing layer, the active agent impermeable backing layer supported on the outer patch release layer overlying the opening therein, the active agent layer containing an active agent for administration to the skin or mucosa of a host;
    wherein a portion of the active agent impermeable backing layer of the inner patch is adhered directly to the adhesive layer exposed through the opening prior to and after removal of the outer patch release layer for application of the device to the skin or mucosa of a host; and
    wherein a remaining portion of the active agent impermeable backing layer is unadhered to the adhesive layer as a result of the outer patch release layer being interposed therebetween prior to removal for application of the device to the skin or mucosa of a host, wherein the outer patch has a surface area greater than a surface area of the inner patch, such that removal of the outer patch release layer for application of the device adheres the remaining portion of the active agent impermeable backing layer directly to a portion of the adhesive layer of the outer patch while exposing another portion of the adhesive layer of the outer patch extending beyond a periphery of the inner patch for adhering the device to the skin or mucosa of a host.

2. The device of claim 1, wherein the active agent layer of the inner patch includes a pressure-sensitive adhesive for adhering the device to the skin or mucosa of a host.

3. The device of claim 1, further including a layer of active agent permeable adhesive applied overlying the active agent layer of the inner patch for adhering the device to the skin or mucosa of a host.

4. The device of claim 1, wherein at least a portion of the outer patch includes an active agent to be administered to the skin or mucosa of a host.

5. The device of claim 1, wherein the active agent is an analgesic.

6. The device of claim 1, further including an outer patch release layer releasably adhered to the active agent layer of the inner patch.

7. The device of claim 1, wherein the outer patch release layer is coextensively adhered to the adhesive layer of the outer patch.

8. A storage-stable device for the release of an active agent to the skin or mucosa of a host, the device comprising:
    an outer patch comprising a top surface having peripheral edges and an opposing bottom surface, the outer patch having adhesive properties for adhering the top surface to the skin or mucosa of a host;
    an outer patch release layer of an active agent impermeable material releasably adhered to the top surface of the outer patch, the outer patch release layer having a surface area and shape to extend to at least the peripheral edges of the top surface, the outer patch release layer having an opening exposing a portion of the top surface of the outer patch;
    an inner patch comprising an active agent layer supported on a co-extensive active agent impermeable backing layer, the active agent layer containing an active agent for administration to the skin or mucosa of a host, the active agent impermeable backing layer supported directly on the outer patch release layer with a portion of the active agent impermeable backing layer bonded directly to a portion of the top surface of the outer patch exposed through the opening in the outer patch release layer prior to and after removal of the outer patch release layer for application of the device to the skin or mucosa of a host, a surface area of the opening being smaller than a surface area of the inner patch; and
    whereby the inner patch has an annular portion surrounding the opening which is not adhered to the top surface of the outer patch as a result of a portion of the outer patch release layer being interposed therebetween prior to removal for application of the device to the skin or mucosa of a host, wherein the outer patch has a surface area greater than a surface area of the inner patch, such that removal of the outer patch release layer for application of the device adheres the annular portion of the inner patch directly to an annular portion of the top surface of the outer patch while exposing a portion of the top surface of the outer patch extending beyond a periphery of the inner patch for adhering the device to the skin or mucosa of a host.

9. The storage-stable device of claim 8, wherein the active agent layer is defined by peripheral edges, and wherein the peripheral edges of the active agent layer are separated from the top surface of the outer patch by a portion of the outer patch release layer interposed therebetween prior to removal for application of the device to the skin or mucosa of a host.

10. The device of claim 8, wherein the active agent layer of the inner patch includes a pressure-sensitive adhesive for adhering the device to the skin or mucosa of a host.

11. The device of claim 8, further including a layer of active agent permeable adhesive applied overlying the active agent layer of the inner patch for adhering the device to the skin or mucosa of a host.

12. The device of claim 8, wherein at least a portion of the outer patch includes an active agent to be administered to the skin or mucosa of a host.

13. The device of claim 8, wherein the active agent is an analgesic.

14. The device of claim 8, further including an outer patch release layer releasably adhered to the active agent layer of the inner patch.

15. The device of claim 8, wherein the outer patch release layer is coextensively adhered to the top surface of the outer patch.

\* \* \* \* \*